United States Patent [19]
Hollister

[11] Patent Number: 5,232,454
[45] Date of Patent: Aug. 3, 1993

[54] SAFETY NEEDLE CONTAINER

[75] Inventor: William H. Hollister, Keene, N.H.

[73] Assignee: Smiths Industries Medical Systems, Inc., Keene, N.H.

[21] Appl. No.: 561,459

[22] Filed: Aug. 1, 1990

[51] Int. Cl.$^5$ .............................................. A61M 5/32
[52] U.S. Cl. .................................. 604/192; 604/263; 604/110
[58] Field of Search ............... 604/110, 162, 167, 192, 604/198, 263

[56] References Cited

U.S. PATENT DOCUMENTS

| | | |
|---|---|---|
| 1,779,451 | 10/1930 | Sponsel . |
| 2,700,385 | 1/1955 | Ortiz . |
| 2,836,942 | 6/1958 | Miskel . |
| 2,854,976 | 10/1958 | Heydrich . |
| 2,953,243 | 9/1960 | Roehr . |
| 3,021,942 | 2/1962 | Hamilton . |
| 3,073,307 | 1/1963 | Stevens . |
| 3,074,542 | 1/1963 | Myerson et al. . |
| 3,255,873 | 6/1966 | Speelman . |
| 3,294,231 | 12/1966 | Vanderbeck . |
| 3,323,523 | 6/1967 | Scislowicz et al. . |
| 3,324,853 | 6/1967 | Czorny et al. ............ 604/162 |
| 3,329,146 | 7/1967 | Waldman, Jr. . |
| 3,333,682 | 8/1967 | Burke . |
| 3,367,488 | 2/1968 | Hamilton . |
| 3,485,239 | 12/1969 | Vanderbeck . |
| 3,537,452 | 11/1970 | Wilks . |
| 3,610,240 | 10/1971 | Harautuneian . |
| 3,658,061 | 4/1972 | Hall . |
| 3,828,775 | 8/1974 | Armel . |
| 3,890,971 | 6/1975 | Leeson et al. . |
| 3,904,033 | 9/1975 | Haerr . |
| 3,934,722 | 1/1976 | Goldberg .................... 206/365 |
| 3,968,876 | 7/1976 | Brookfield . |
| 4,113,090 | 9/1978 | Carstens .................... 206/365 |
| 4,139,009 | 2/1979 | Alvarez . |
| 4,175,008 | 11/1979 | White . |
| 4,300,678 | 11/1981 | Gyure et al. ............... 206/364 |
| 4,375,849 | 3/1983 | Hanifl ........................ 206/366 |
| 4,430,082 | 2/1984 | Schwabacher ............. 604/263 |
| 4,592,744 | 6/1986 | Jagger et al. ............... 604/192 |
| 4,634,428 | 1/1987 | Cuu ............................ 604/110 |
| 4,643,722 | 2/1987 | Smith, Jr. ................... 604/192 |
| 4,659,330 | 4/1987 | Nelson et al. .............. 604/192 |
| 4,664,259 | 5/1987 | Landis ........................ 604/192 |
| 4,664,654 | 5/1987 | Strauss ....................... 604/198 |
| 4,681,567 | 7/1987 | Masters et al. ............. 604/198 |
| 4,695,274 | 9/1987 | Fox ............................. 604/198 |
| 4,702,738 | 10/1987 | Spencer ...................... 604/198 |

(List continued on next page.)

FOREIGN PATENT DOCUMENTS

| | | |
|---|---|---|
| 1233302 | 5/1971 | United Kingdom . |
| 87/07162 | 12/1987 | World Int. Prop. O. . |
| 9001348 | 2/1990 | World Int. Prop. O. . |

Primary Examiner—C. Fred Rosenbaum
Assistant Examiner—Ronald K. Stright, Jr.
Attorney, Agent, or Firm—Pollock, Vande Sande & Priddy

[57] ABSTRACT

A universal safety adapter usable with different types of needles and syringes has integral first and second portions and a housing, including an integral compressible section connecting a main body section to an end cap section, flexibly connected to one of the portions. In the case of the first portion being mated to the hub of a needle assembly, the housing is flexibly connected thereto by a living hinge. Once the needle assembly has been mated to the first portion of the safety adapter, to preclude accidental pricking by the needle after use, the housing is pivoted to a position whereby it completely envelops the cannula. To provide additional protection, the end cap section, which has adapted thereto an elastomer, may be urged longitudinally toward the main body section so that the tip of the contaminated needle is completely encased by the elastomer as the compressible section collapses under pressure. The dead space volume at the junction where the needle is connected to the syringe can be substantially reduced by a second embodiment of the safety adapter of the present invention which includes a male extension within the female luer.

57 Claims, 7 Drawing Sheets

U.S. PATENT DOCUMENTS

| | | | |
|---|---|---|---|
| 4,723,943 | 2/1988 | Spencer | 604/198 |
| 4,728,320 | 3/1988 | Chen | 604/110 |
| 4,728,321 | 3/1988 | Chen | 604/110 |
| 4,731,059 | 3/1988 | Wanderer et al. | 604/192 |
| 4,735,311 | 4/1988 | Lowe et al. | 206/365 |
| 4,735,618 | 4/1988 | Hagan | 604/198 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,747,836 | 5/1988 | Luther | 604/198 |
| 4,747,837 | 5/1988 | Hauck | 604/198 |
| 4,772,272 | 9/1988 | McFarland | 604/198 |
| 4,778,453 | 10/1988 | Lopez | 604/110 |
| 4,781,697 | 11/1988 | Slaughter | 604/192 |
| 4,782,841 | 11/1988 | Lopez | 604/198 |
| 4,790,828 | 12/1988 | Dombrowsk et al. | 604/198 |
| 4,795,432 | 1/1989 | Karczmer | 604/110 |
| 4,795,443 | 1/1989 | Permenter et al. | 604/198 |
| 4,801,295 | 1/1989 | Spencer | 604/198 |
| 4,804,372 | 2/1989 | Laico et al. | 604/198 |
| 4,813,426 | 3/1989 | Haber et al. | 604/232 |
| 4,816,022 | 3/1989 | Poncy | 604/263 |
| 4,816,024 | 3/1989 | Sitar et al. | 604/192 |
| 4,819,659 | 4/1989 | Sitar | 604/198 |
| 4,820,277 | 4/1989 | Norelli | 604/192 |
| 4,826,490 | 5/1989 | Byrne et al. | 604/198 |
| 4,826,491 | 5/1989 | Schramm | 604/198 |
| 4,838,871 | 6/1989 | Luther | 604/192 |
| 4,842,587 | 6/1989 | Poncy | 604/198 |
| 4,846,796 | 7/1989 | Carrell et al. | 604/110 |
| 4,850,968 | 7/1989 | Romano | 604/110 |
| 4,850,976 | 7/1989 | Heinrich et al. | 604/192 |
| 4,850,977 | 7/1989 | Bayless | 604/198 |
| 4,850,978 | 7/1989 | Dudar et al. | 604/201 |
| 4,850,994 | 7/1989 | Zerbst et al. | 604/198 |
| 4,850,996 | 7/1989 | Cree | 604/198 |
| 4,858,607 | 8/1989 | Jordan et al. | 128/314 |
| 4,863,434 | 9/1989 | Bayless | 604/198 |
| 4,863,435 | 9/1989 | Sturman et al. | 604/198 |
| 4,863,436 | 9/1989 | Glick | 604/198 |
| 4,867,746 | 9/1989 | Dufresne | 604/192 |
| 4,872,552 | 10/1989 | Unger | 206/365 |
| 4,874,383 | 10/1989 | McNaughton | 604/263 |
| 4,874,384 | 10/1989 | Nunez | 604/198 |
| 4,883,469 | 11/1989 | Glazier | 604/192 |
| 4,886,503 | 12/1989 | Miller | 604/192 |
| 4,888,001 | 12/1989 | Schoenberg | 604/192 |
| 4,892,107 | 1/1990 | Haber | 604/198 |
| 4,892,521 | 1/1990 | Laico et al. | 604/192 |
| 4,900,309 | 2/1990 | Netherton et al. | 604/192 |
| 4,932,946 | 6/1990 | Shields | |
| 4,950,242 | 8/1990 | Alvarez | 604/110 |
| 4,982,842 | 1/1991 | Hollister | 604/192 |

SAFETY NEEDLE CONTAINER

FIELD OF THE INVENTION

This invention is related to copending application entitled "Safety Needle Container", filed Jun. 4, 1990, by the same inventor, and assigned to the same assignee, as the instant invention. Specifically, it relates to hypodermic needles and more particularly to a safety device for housing a hypodermic needle and sealing the tip of the needle to ensure that a person will not be accidentally pricked by the needle, particularly after the needle has been used and is to be disposed of.

BACKGROUND OF THE INVENTION

In handling a hypodermic needle, there is always a chance that the user, or persons in the proximity of the needle, may be exposed to accidental pricking thereby. And in view of the current crop of infectious diseases, particularly the as yet incurable Acquired Immune Deficiency Syndrome (AIDS), an urgent need exists to provide a safety device for preventing accidental pricking by a needle, especially one that has been used and is therefore contaminated.

There are in the prior art a number of safety devices for guarding a needle, or more precisely its cannula, so that its sharp end will not be exposed. For example, Sponsel U.S. Pat. No. 1,779,451 discloses a syringe that has a needle guide pivotable at a point about the syringe casing for guarding the needle. Scislowicz U.S. Pat. No. 3,323,523 discloses a sheath formed of two portions that can pivot about respective hinges to cover a cannula. Moreover, the sheath may be locked by having a sleeve slid thereover. Hall U.S. Pat. No. 3,658,061 discloses a catheter needle guard unit that may be pivoted to snap over the needle. The sheath, once snapped, may be unsnapped since it is not locked onto the needle. Smith, Jr. U.S. Pat. No. 4,643,722 discloses a hypodermic needle assembly that has a closure having an elongated slot which enables the closure to be either removed from or inserted toward the hypodermic needle. The Smith device requires two-handed operation. Furthermore, no locking means is disclosed. Nelson et al. U.S. Pat. No. 4,659,330, on the other hand, discloses a needle protective cap which is slidable, by means of a clip, along the body of the syringe. The needle cover, however, may be completely removed from the needle.

Additional slidable needle protectors are disclosed in Spencer U.S. Pat. Nos. 4,702,738 and 4,723,943 wherein a protective sheath is shown to be slidable along a syringe body. Yet other needle covers that are slidable along a syringe body are disclosed in Choksi U.S. Pat. No. 4,737,144 and Schneider U.S. Pat. No. 4,743,233. Some other example devices having protective sheaths for needles include Laico et al. U.S. Pat. No. 4,804,372; Poncy U.S. Pat. No. 4,816,022; Schramm U.S. Pat. No. 4,826,491; Poncy U.S. Pat. No. 4,842,587; Carrell et al. U.S. Pat. No. 4,846,796; Romano U.S. Pat. No. 4,850,968; Bayless U.S. Pat. No. 4,850,977; Zerbst et al. U.S. Pat. No. 4,850,994; Cree U.S. Pat. No. 4,850,996; Jordan et al. U.S. Pat. No. 4,858,607; Bayless U.S. Pat. No. 4,863,434 and Haber U.S. Pat. No. 4,892,107. As is readily apparent, all of these devices having covers that are slidable along the length of the syringe body require two-handed operation.

Another type of prior art needle protective device involves the pivoting of a needle sheath to cover the cannula of the needle assembly. Some prior art examples of this type of device include Norelli U.S. Pat. No. 4,820,277 wherein a pair of jaws is disclosed as pivotable and lockable over a needle. As is readily apparent, however, the Norelli cover also requires two-handed operation. Glazier U.S. Pat. No. 4,883,469 discloses a guard assembly that is coupled to a sheath by a fastener and is rotatable about a hinge to snap onto the needle. The sheath, along with the pivotable guard, has to be preassembled with the needle for a specific type of syringe. Schoenberg U.S. Pat. No. 4,888,001 discloses a longitudinal shank having two flat wings which are pivotable to enclose the sharp distal end of the needle. None of these prior art devices appears to disclose the permanent retention of the needle by the protective sheath once the protective sheath has been pivoted to enclose the needle.

There are a couple of prior art safety devices that do teach the permanent retention of a needle within the housing once it has been enclosed thereby. Landis U.S. Pat. No. 4,664,259 is one such which discloses a needle assembly that includes a pivotable housing having therein a hook to retain the needle within the housing after the housing has been pivoted to enclose the needle. The Landis device, however, comes in a unitary package, inasmuch as the needle is integrated into the base, which in turn has connected thereto the pivotable housing. Unger U.S. Pat. No. 4,872,552 also discloses a pivotable housing integrated into a needle. In one of the embodiments, the Unger housing is threaded to a specific type of needle housing hub. To lock the housing permanently to the needle, a plug has to be pushed from the top of the housing longitudinally (along the length of needle) into the housing until the tip of the needle rests within the plug. To operate the Unger device, a user has to first pivot the housing into alignment with the needle, hold the housing to maintain alignment of the needle therewith and then push the plug flush with the end of the housing in order to lock the needle within the housing. Needless to say, there is always a chance that if the user is not careful in maintaining the needle within the housing before pushing the plug flush to the end of the housing, the tip of the needle may remain exposed; and, therefore, the user may actually be moving his hand/finger directly into contact with the needle.

Inasmuch as there is available in the market a number of different types of needles and syringes, there is a need to have a universal safety device that is adaptable to be used with the different types of needles and syringes. And it is imperative that such safety device be amendable to single-handed operation, as for example during emergency room situations where a user may have only one hand free. Furthermore, to provide extra protection to ensure that the tip of the needle, especially after use, is not exposed, some means must be used to seal the same.

Finally, it has been found that oftentimes there is a large unused and therefore wasteful volume of space at the junction where the syringe and needle are joined which has to be filled with blood to be drawn from or fluid to be injected into a patient.

SUMMARY OF THE PRESENT INVENTION

The safety device of the present invention is a stand alone adapter that has a male and female end for mating with a needle assembly and the ejection end of a syringe, respectively. There is flexibly connected to the portion of the adapter that is to be mated with the needle assembly a housing/sheath which is pivotable to a position in alignment with the needle for enveloping the same. Within the housing is at least one confining means for retaining the needle within the housing once the housing has been pivoted into the alignment position.

For this invention, the housing comprises a main body section, an end cap section and a non-limiting accordion-shaped compressible section integrally connecting the main body and end cap sections. The compressible section may be made thinner than the main body and the end cap sections so as to be compressible, collapsible or crushable when the main body and end cap sections are urged relatively toward each other.

The portion of the adapter to be mated with the needle assembly includes a male luer that is surrounded by an internally threaded annular collar, which is to mate with the hub of the needle assembly. There is extending from a portion of the annular collar a shoulder member, which has connected to its distal end, by way of a living hinge, the housing.

The housing has an elongated slot formed longitudinally along at least the entire length of the main body section, and possibly partway along the compressible section, which may be so configured that its side through which the slot would have extended is open to the environment.

When a needle assembly, via its hub, is threaded to the annular collar to mate with the male luer, the elongated slot is aligned to face the needle (or cannula) so that the needle would pass therethrough, as the housing is pivoted about the shoulder member to enclose the needle.

Integral of the housing is a resilient hook member which gives way to the needle when the housing is pivoted into its alignment position, but which, once the needle is in place, forms a secure fastener for permanently retaining the needle within the housing. To ensure that the present invention safety adapter is adaptable for all types of needles having different lengths, a plurality of retaining means may be integrated into the housing of the adapter.

To minimize the chances of the tip of the needle becoming exposed, as for example in the unlikely event that the housing cracks after it has been pivoted to envelop the needle, adapted to the end cap section is an elastomeric material, such as rubber, which may be urged against the tip of the needle to be penetrated thereby. The urging of the elastomer toward the needle is effected by the relative movement of the end cap and main body sections toward each other, which in turn causes the compressible section to be either collapsed, crushed or retracted. As a consequence, the tip of the needle is sealingly secured within the elastomer. Thus, with the housing completely enveloping and retaining the needle and the tip of the needle being firmly gripped by the elastomer, the chances that a person may be accidentally pricked by the needle are greatly reduced.

In place of the compressible section, a combination hinge and crushable (collapsible or compressible) section may be used. Thus, instead of moving the end cap and main body sections of the housing relative to each other, the housing itself is pushed toward the base of the adapter, which is connected to the housing by the combination hinge and crushable section. Of course, no compressible section is required in the housing for this alternative embodiment since the end cap section of the housing integrally extends from the main body section of the same. As its name implies, with a compressive force applied thereagainst, the hinge and crushable section collapses, thereby allowing the tip of the needle to pierce and be retained by the elastomer within the end cap section of the housing.

In view of the end cap section and the elastomer which, in combination, provide permanent locking of the needle, in place of the resilient hook member, two resilient extensions together forming a forked member may instead be used to only frictionally retain the needle—before the end cap section is pushed toward the main body section—as the needle is snappedly inserted between the extensions when the housing is pivoted into alignment with the needle.

A first preferred embodiment of the safety device of the present invention has the end of the adapter that is to be mated to the male luer of the syringe containing only a female luer, so that the male luer, i.e., the ejection end, of the syringe may be slip-fittedly mated with the adapter. There is disposed at the distal end and perpendicularly to the longitudinal length of the adapter at least one extension for threadedly locking the female luer of the adapter to the male luer of a syringe, if the syringe is a luer lock type that has an internally threaded annular collar surrounding the male luer.

A second preferred embodiment of the adapter of the present invention has a male member within the female luer such that the volume of space through which fluid transits between the syringe and the needle is substantially reduced.

To operate, after the needle has been used, inasmuch as the housing is flexibly attached to the safety adapter, by pushing against some solid object, the housing can be pivoted about and securely retain the contaminated needle. To ensure that the tip of the contaminated needle is not exposed even under unforseen circumferences, the elastomer is urged against the needle so that the latter's tip penetrates into the former and is gripped sealingly and firmly thereby. The urging of the elastomer can of course be effected by pushing the end cap section of the housing against some immobile object to compress or collapse the compressible section to thereby push the needle into the elastomer. Thus, the safety adapter of the present invention requires only single-handed operation.

It is, therefore, an objective of the present invention to provide a universal safety adapter that is adaptable to mate with all types of needles and syringes.

It is another objective of the present invention to provide a safety adapter that does not require two-handed operation.

It is yet another objective of the present invention to provide a safety adapter that can substantially reduce the volume of dead space through which fluid transits between the syringe and the needle.

It is yet a further object of the present invention to provide a safety adapter that can sealingly secure the tip of the needle.

BRIEF DESCRIPTION OF THE FIGURES

The above-mentioned objectives and advantages of the present invention will become more apparent and the invention itself will be best understood by reference to the following description of embodiments of the present invention taken in conjunction with the accompanying drawings, wherein.

DETAILED DESCRIPTION OF THE INVENTION

Figures 1A, 1B:
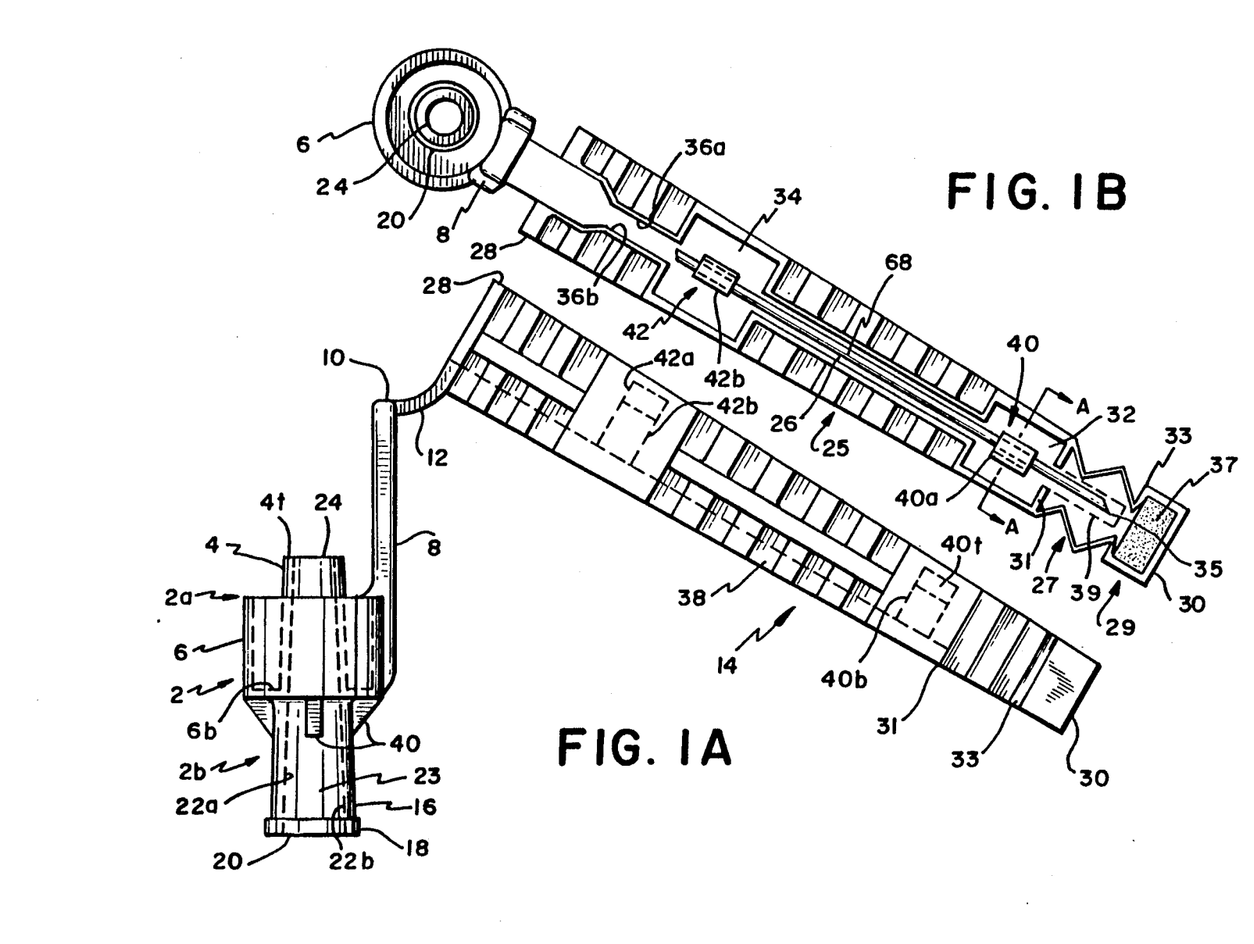
FIG. 1A is a side view of a first embodiment of the present invention safety adapter.
FIG. 1B is a plan view of the FIG. 1A embodiment illustrating the retention of a partial needle.

With reference to FIG. 1A, there is shown a safety needle adapter having a base 2 with a first section 2a and a second section 2b. Both sections 2a and 2b are integral of one-piece molded base 2.

Figures 2A, 2C:
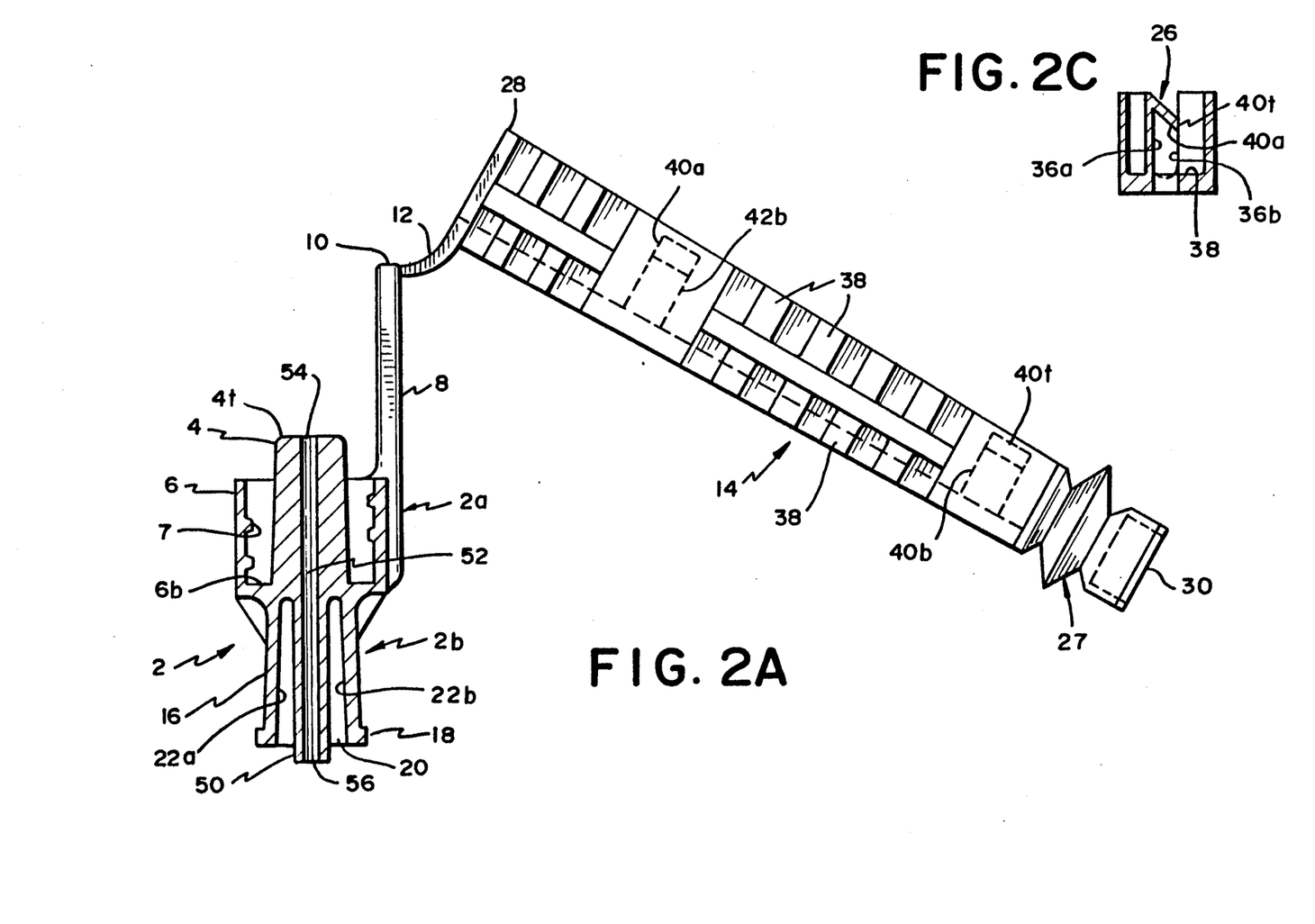
FIG. 2A is a semicross-sectional view of another embodiment of the safety adapter of the present invention.
FIG. 2C is a cross-sectional view shown along section A—A in FIG. 2B.

Section 2a includes a central protrusion 4, conventionally known as a male luer. Surrounding protrusion 4 is an annular collar 6, extending from approximately the midsection of base 2. Collar 6, although not shown as such in FIG. 1A, in practice, is internally threaded, as shown in FIG. 2A. Extending from a portion of collar 6 is a substantially rigid shoulder member 8. Connected to distal end 10 of shoulder member 8, by a living hinge 12, is a housing 14.

Section 2b extends approximately from the midsection of base 2 away from collar 6, as a hub or extension 16. At the distal end of hub 16 is, for this embodiment, a circumferential extension 18, extending orthogonally to the longitudinal length of base 2, for mating with the internal threads of a syringe. See FIG. 4. It should be appreciated that instead of a ring-like extension, 18 may actually be comprised of a plurality of singular extensions. There is formed at the base of hub 16 an opening 20 which extends in a decreasingly tapered fashion along dotted lines 22a and 22b to the top of protrusion 4 to meet with an opening 24. Conventionally, hub 16 may be considered the female luer portion of the adapter of the present invention.

Figures 1C, 1D, 1E:
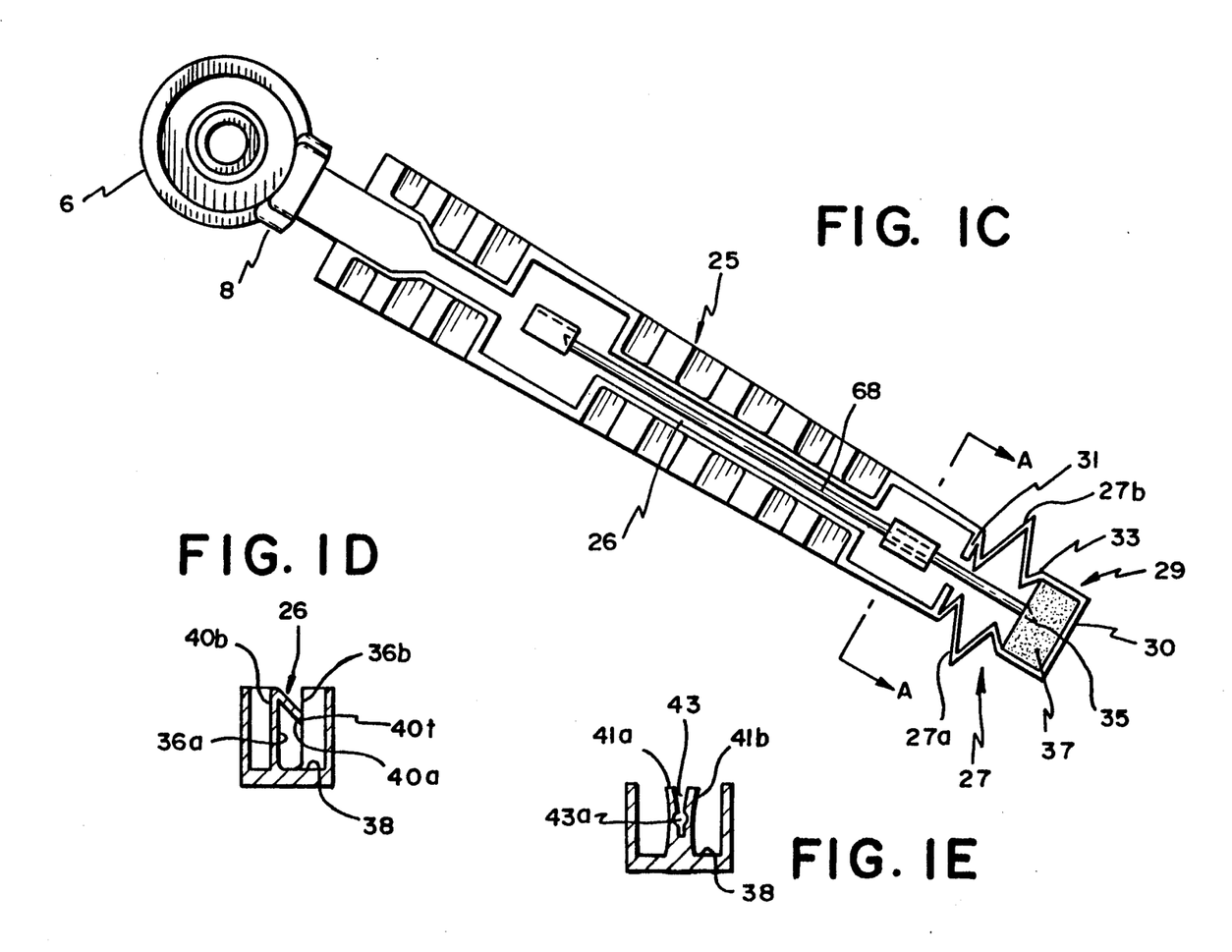
FIG. 1C is another plan view of the FIG. 1A embodiment showing the tip of the partial needle having penetrated an elastomer adapted to the end cap section of the housing.
FIG. 1D is a cross-sectional view of section A—A noted in FIG. 1B illustrating one type of retaining means.
FIG. 1E is a cross-sectional view of section A—A noted in FIG. 1B illustrating another type of retaining means.

With reference to the plan views of FIGS. 1B and 1C, housing 14 comprises a main body section 25, an accordion-like compressible, retractable or crushable section 27 and an end cap (capped end) section 29. For purposes of explanation, main body section 25 extends from end 28 of housing 14 to a partition 31; compressible section encompasses the section from partition 31 to edge 33; and end cap section 29 extends from edge 33 to tip 30.

As shown, main body section 25 is connected to end cap section 29 by compressible section 27, which may be an integral part of housing 14, if housing 14 is a single piece molded sheath, manufactured for example from plastic. In which case, compressible section 27 may be made thinner than main body section 25 and/or end cap section 29. Alternatively, compressible section 27 may be made of materials different from that of main body section 26, or end cap section 29. For example, a perfectly acceptable alternative compressible section 27 may be made from either foldable cardboard or fibered paper, or some other material proven not easily pierced by the tip of a needle, sandwiched by and bondedly connecting main body section 25 and end cap section 29.

Although compressible section 27 is shown in FIGS. 1B and 1C as accordion-shaped, it should be appreciated that other shapes may also be used as long as compressible section 27 is retractable so that the distance separating main body section 25 and end cap section 29, (i.e. the distance from partition 31 to edge 33) may be reduced, as relative movement urging sections 25 and 29 toward each other is effected.

Adapted to and fitted within end cap section 29 is an elastomeric material 37 which may be, for example, a malleable elastomer, a piece of rubber or some other suitable material which can sealingly secure and firmly grip some sharp instrument penetrating therein, as for example tip 35 of needle 68. Materials such as cork or wax may also be used.

Figure 3:
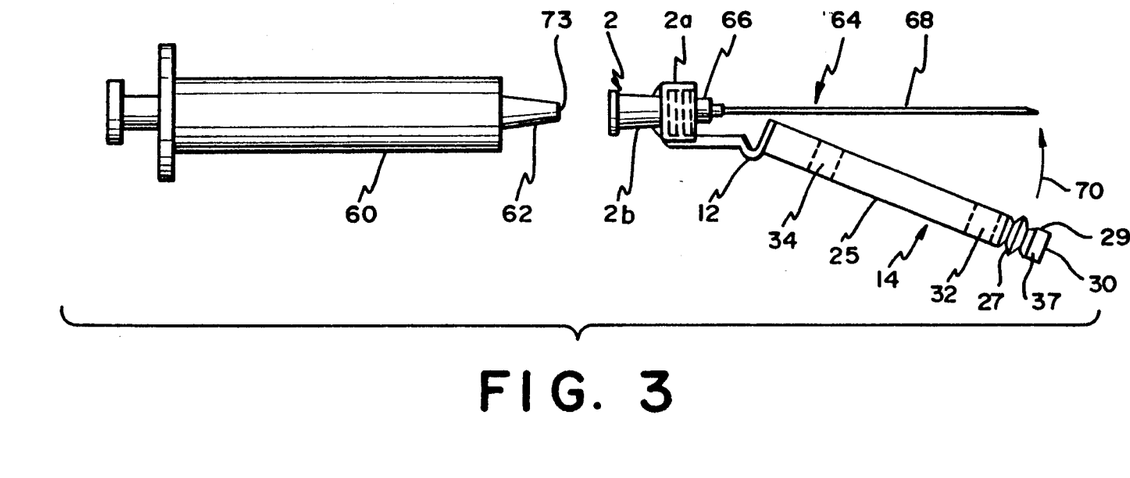
FIG. 3 is an overall view of the safety adapter of the present invention being used with a luer slip type syringe.
Figure 4:
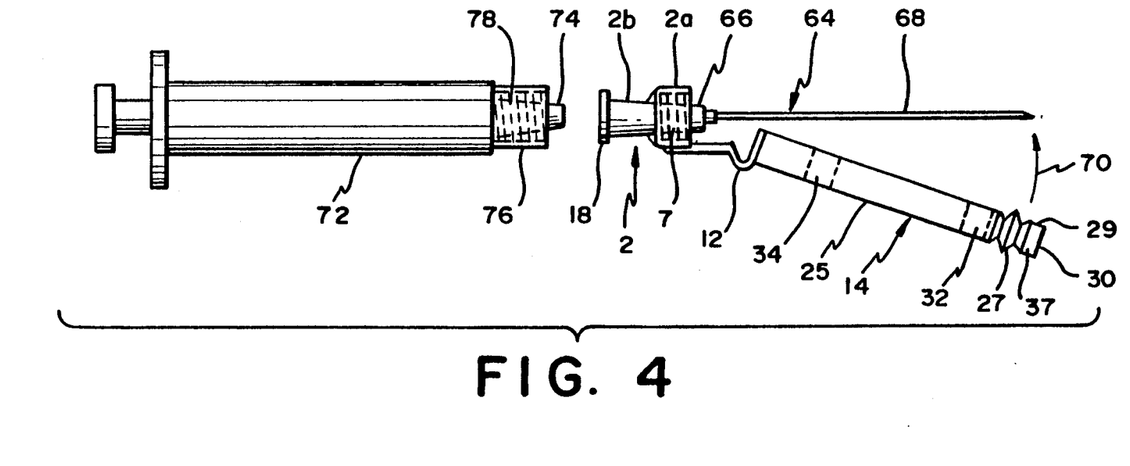
FIG. 4 is an overall view of the safety adapter of the present invention being used with a luer lock type syringe.

By connecting housing 14 via living hinge 12 to shoulder member 8, housing 14 is pivotable about distal end 10 of shoulder member 8, such that it comes into an alignment position about the longitudinal axis of the cannula (which also happens to be the longitudinal axis of base 2) of a needle assembly, as shown and to be discussed in FIGS. 3 and 4.

There is shown in greater detail in FIG. 1B an elongated slot 26 running from base 28 of housing 14 along the length of main body section 25 of housing 14 to partition 31. As most clearly shown by dotted outline 39 in FIGS. 1B and 2B, elongated slot 26 may be extended beyond main body section 25 partway along compressible section 27. This is the case if compressible section 27 is fully enclosed. In the case where compressible section 27 is semi-enclosed per shown in FIG. 1C, no such elongated slot is needed since the side of compressible section 27 through which the cannula passes is unobstructed.

Tip 30 of end cap section 29 preferably is made of a material such as hard plastic that is substantially impervious to penetration by sharp instruments, for example tip 35 of needle 68. The length of housing 14—more specifically the distance from end 28 through slot 26, or to the top of potential slot 39 (if compressible section 27 is fully-enclosed as in FIG. 1B)—is such that clearance is provided for a needle of any available length in the market to pass therethrough when housing 14 is pivoted to encircle the needle. In the case where compressible section 27 is semi-enclosed, the distance from end 28 to edge 33 of housing 14 provides the necessary clearance.

As shown in FIG. 1B, there is an opening 32 located proximately to one end of main body section 25, adjacent to partition 31, and another opening 34 located close to base 28 of housing 14. With reference also to FIG. 1D, it can be seen that slot 26 is bounded by sides 36a and 36b, running substantially in parallel along the length of housing 14, and a bottom 38. At the center of respective openings 32 and 34 there are integral of housing 14 corresponding hook-like retaining mechanisms 40 and 42.

As best shown in FIG. 1D with reference only to retaining mechanism 40, a substantially rigid finger 40a extends in a downward slope fashion from the apex of extension 40b, molded to bottom 38. It should be appreciated that, although substantially rigid, finger 40a may be biased by the cannula of a needle assembly toward extension 40b until the cannula is past tip 40t thereof, at which time finger 40a would flex back into the position shown in FIG. 1D, thereby permanently retaining the cannula within the space defined between finger 40a and extension 40b to prevent the cannula from moving relative to housing 14.

Retainer mechanism 42 is the same as retainer mechanism 40 except, as shown in FIG. 1B, its finger portion 42b slopes downward toward side 36b of housing 14. In contrast, finger 40a of retaining mechanism 40 is shown to be sloping downward toward side 36a in the housing. By thus transposing the finger portions of the respective retaining mechanisms, it becomes more difficult for the cannula of the needle assembly to be forcibly removed from the housing, were the cannula being retained by both retaining mechanisms.

An alternative retaining mechanism for frictionally retaining the cannula of the needle assembly is shown in FIG. 1E. This alternative retaining mechanism can be used in conjunction with elastomer 37 adapted to end cap section 29 to fully prevent movement of a needle, relative to housing 14.

As shown in FIG. 1E, the alternative retaining mechanism is forked-shaped and comprises two semi-rigid resilient extensions 41a and 41b. The space between extension 41a and 41b, designated 43, is of such a size that once a needle is forcibly urged thereinto, it will be frictionally held by extensions 41a and 41b. An enlarged opening 43a may be effected in space 43 to accommodate and align needle 68. Although not providing the same retentiveness as the retention mechanism shown in FIG. 1D, the FIG. 1E retention mechanism provides sufficient retention when used in conjunction with an end cap section having an elastomer, as will be discussed later.

To provide strength for the housing, a plurality of ribs 38 is provided along the length of housing 14. Likewise, to provide strength and rigidity to base 2 such that it would not crack even if it were subjected to undue bending moment at base 6b, a number of buttress ribs 40 slanting upward from hub 16 to base 6b of annular collar 6 is provided.

Figure 2B:
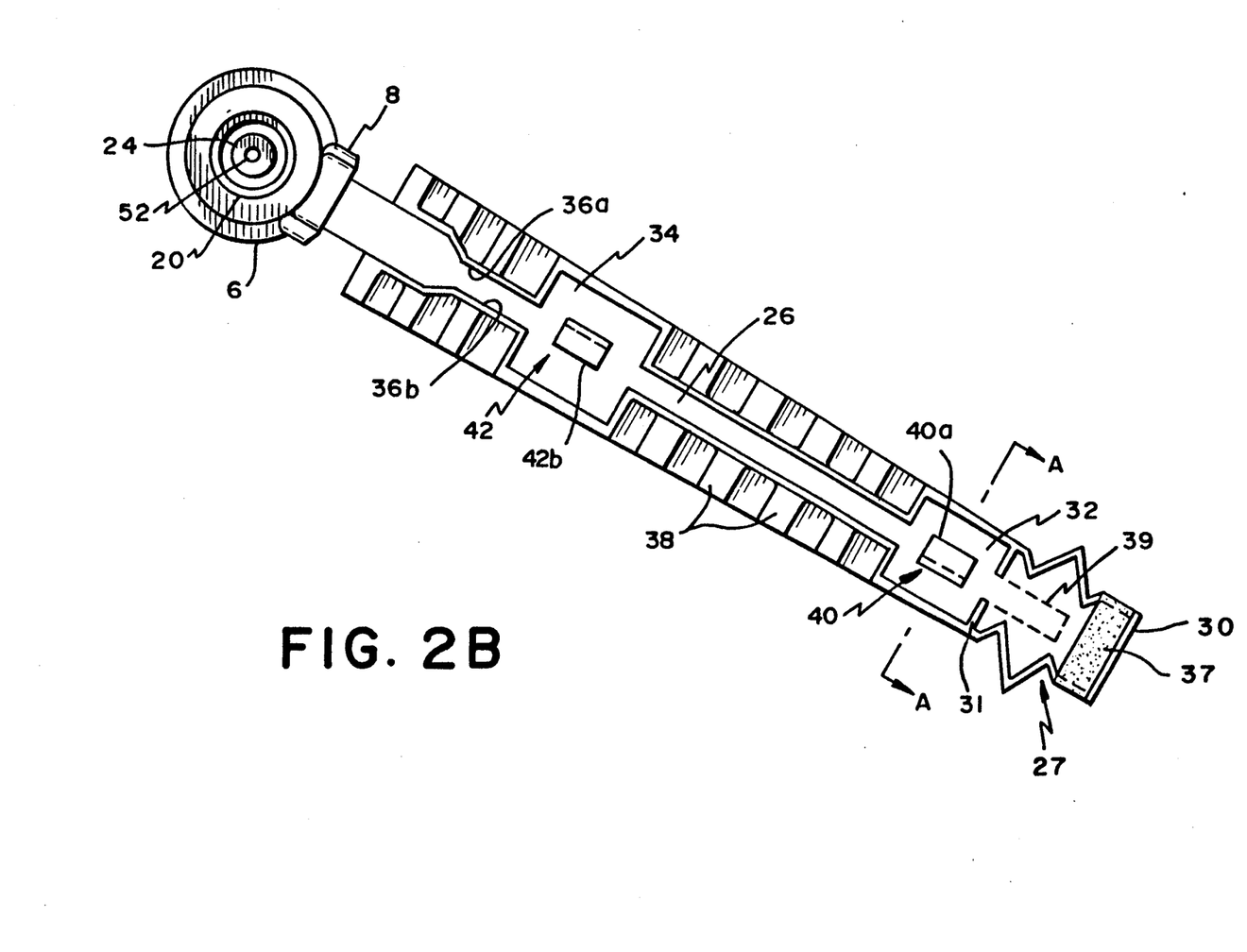
FIG. 2B is a plan view of the FIG. 2A embodiment.

A second preferred embodiment of the safety adapter of the present invention is illustrated in FIGS. 2A, 2B and 2C. For these figures, components which are the same as the components shown in FIGS. 1A to 1E, or perform essentially the same functions, are labeled the same.

Like the first embodiment, the FIG. 2 embodiment has base 2 connected, by shoulder member 8 and living flexible hinge 12, to housing 14, which is likewise divided into the same sections as shown in FIGS. 1A to 1C. This embodiment, however, is directed to substantially reducing the volume of space through which a fluid—be it blood or medicament—transits between the syringe and the needle, as for example when blood is being drawn from a patient to the syringe or when a medicament in the syringe is being intravenously fed to the patient via the needle.

To achieve this end, the embodiment of FIG. 2A has incorporated into base 2, particularly at section 2b, a conical extension (i.e., a snout or male luer) 50 extending from approximately base 6b to beyond the plane of hole 20 at the base of the adapter. Furthermore, instead of having a through bore such as 23 shown in FIG. 1A extending from top hole 24 to bottom hole 20 and confined by sidewalls 22a and 22b and therefore having a substantial amount of dead space, the FIG. 2A embodiment now has a through bore 52 running continuously from top 4t of male luer 4 at opening 54 to the distal end of conical extension 50, at opening 56. The diameter of through bore 52 is to be manufactured to substantially correspond to the typical bore of a typical needle (cannula) of a needle assembly so that fluid transiting between openings 54 and 56 would flow directly into the bore of the cannula, without having to first fill up unnecessary dead space such as shown in FIG. 1A.

The inventor has found that this elimination of dead space, in addition to being attractive to a clinician, in actuality, has the important advantage of not requiring the withdrawal of a larger amount of blood than is necessary, as is done conventionally. To elaborate, ordinarily, for an infant, to withdraw an amount of blood more than is necessary (for example ½ cc) for the requisite tests would be traumatic. Yet, conventionally, a lot more blood than is necessary is in fact withdrawn from the infant, in view of the large amount of dead space between the syringe and the needle, such as exemplified by through bore 23 in FIG. 1A.

With the embodiment shown in FIG. 2A, however, inasmuch as the through bore through which fluid transits has been reduced by conical extension 50, acting effectively as a male extension within female luer 16 at section 2b of base 2, only a minimal necessary amount of blood needs to be drawn. It should be appreciated that the length of conical extension 50 in section 2b, and the length of male luer 4 in section 2a, may be longer or shorter than the respective lengths illustrated in FIG. 2B. Likewise, the length of shoulder member 8 may be lengthened or shortened, so long as it enables housing 14, when pivoted to align along and about the longitudinal axis of the cannula, to be cleared of the hub of the needle assembly to which the cannula is attached.

Figures 5A, 5B:
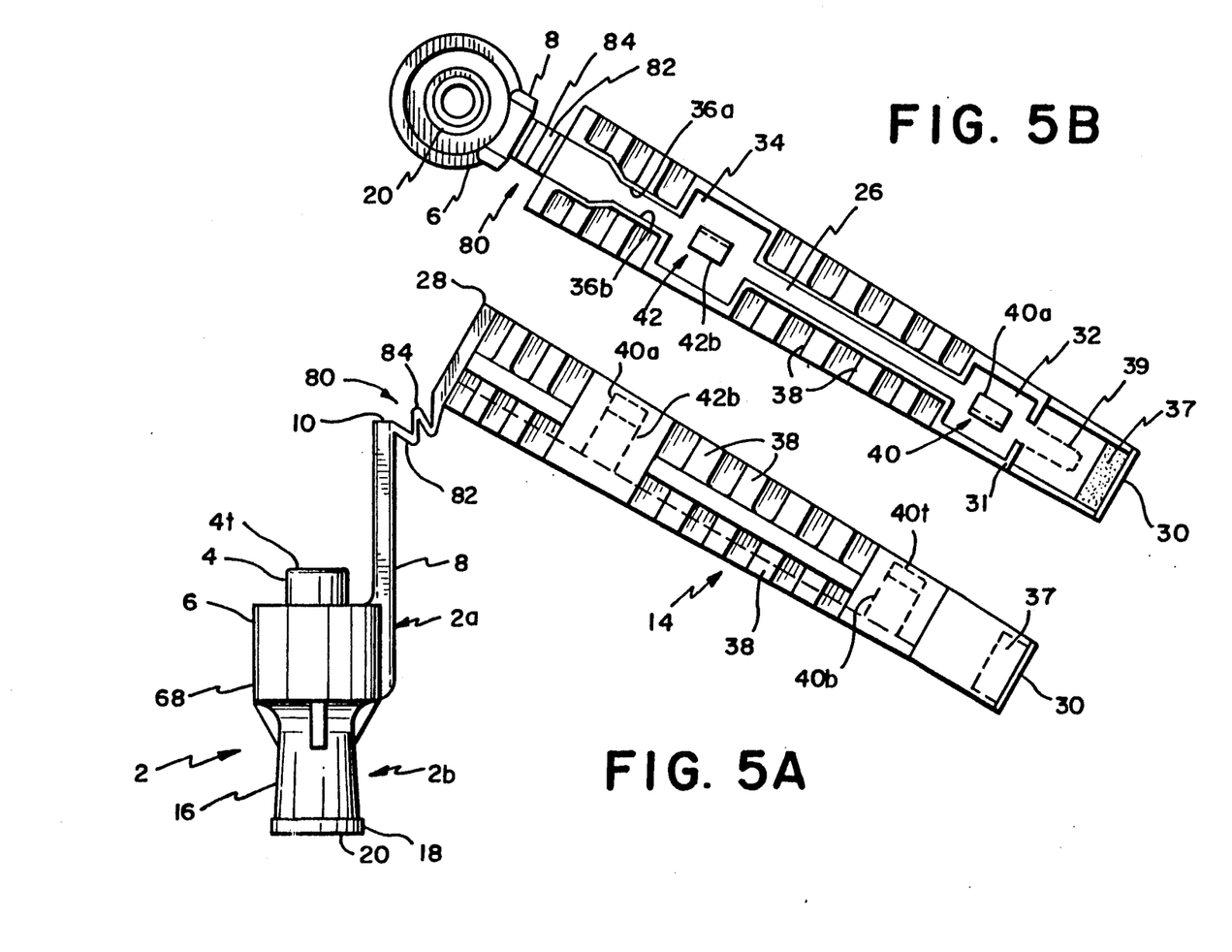
FIG. 5A is a semicross-sectional view of another embodiment of the invention illustrated with a combination hinge and crushable section connecting the base and housing of the adapter.
FIG. 5B is a plan view of the FIG. 5A embodiment.

For the above-discussed embodiment, in place of a housing having a main body section jointed to an end cap section by a compressible section, an alternative method of providing for the secure retention of the tip of a needle is discussed herein with reference to FIGS. 5A and 5B. Components in FIGS. 5A and 5B which are similar or perform similar functions as those discussed earlier are labeled the same.

With reference to FIGS. 5A and 5B it can be seen that housing 14 is a unitary piece extending from end 28 to tip 30. Base 2, as exemplified by the first embodiment base discussed with reference to FIGS. 1A–1C, is flexibly connected to housing 14, at distal end 10 of its shoulder member 8, by a combination hinge and compressible joint 80. As clearly shown in FIG. 5A, joint 80 comprises a plurality of folds 82 (3 shown in FIG. 5A) integrally connecting end 28 of housing 14 to distal end 10 of shoulder member 8. Joint 80 can be made thinner at point 84 during its molding process such that a hinge is formed thereat, thereby allowing housing 14 to be pivoted about point 84 toward base 2 for enveloping the cannula of a needle assembly, as discussed earlier. And inasmuch as joint 80 is accordion-shaped (by way of the plurality of folds 82), once housing has been pivoted to align with base 2, by urging housing 14 and base 2 toward each other, joint 80 can be compressed longitudinally along the length of the cannula to which it envelops.

Although joint 80 has been shown in FIG. 5A as containing only three (3) folds, it should be appreciated that a greater number of folds is possible, as long as the length of shoulder member 8 has been taken into consideration. In other words, shoulder member 8 can be lengthened or shortened, as needed, as long as the combination thereof and joint 80 is such that a cannula of any length can still pass through slot 26.

In operation, with reference to FIGS. 3 and 4, it can be seen that either embodiments of the safety adapter of the instant invention may be mated to a luer slip syringe 60, shown in FIG. 3, that has a male luer ejection end 62. For the FIG. 3 illustration, assuming that the safety adapter embodiment shown in FIG. 1A is used, the user needs only to slip-fittedly insert male luer ejection end 62 into female luer 2b of base 2 for mating. Needle assembly 64, in the meanwhile, is threaded, by means of its hub 66, into annular collar 6. The female luer portion of hub 66 of needle assembly 64 is therefore mated to male luer 4 of base 2, best shown in FIG. 1A. Cannula 68 of needle assembly 64, after use, can be prevented from being exposed and accidentally pricking a person by pivoting housing 14, via living hinge 12 following directional arrow 70, to envelop cannula 68.

As should be readily apparent, when housing 14 is pivoted to align along the longitudinal axis of cannula 68, retaining mechanisms 40 and 42 (see FIGS. 1A, 1B and 1C), upon closing of housing 14 onto cannula 68, will securely retain cannula 68 within housing 14 so that there is no relative movement between housing 14 and cannula 68. It should further be appreciated that, as the length of cannula 68 varies, the fact that there is a plurality of retaining mechanisms integral of housing 14 ensures that the cannula would be retained therein. Alternatively, it should further be appreciated that in place of a plurality of retaining mechanisms, only one retaining mechanism, appropriately positioned somewhere along the length of housing 14, may be used. The relative positioning of the retaining mechanisms along housing 14 is determined, of course, to a great extent, by the length of the to be used cannula.

With specific reference to FIGS. 1B and 1C (where, for the sake of clarity, housing 14 is not being shown as having been pivoted to align with base 2 and cannula 68 is only partially shown), after cannula 68 has been securely retained within housing 14, to ensure that tip 35 of cannula 68 is not exposed (even under highly unlikely and unforseen circumstances) after having been pivoted into alignment with cannula 68, the user may push tip 30 of end cap section 29 against an immobile object, thereby effecting a relative movement of main body section 25 and end cap section 29 toward each other. As compressible section 27 collapses or retracts, elastomer 37 is urged against cannula tip 35 and is pierced thereby. Because of the well known characteristics of an elastomer, as tip 35 penetrates therein, elastomer 37 would sealingly secure and firmly grip the tip of the needle such that it no longer is exposed.

Although not dimensionally shown as such, end cap section 29 and elastomer 37 can be manufactured to have a sufficiently large longitudinal dimension such that the portion of cannula 69 extending past partition 31 can be completely sealed by elastomer 37, due to urging of tip 30 against the immobile object. Putting it differently, compressible section 37 can be crushed to such an extent that end cap section 29 effectively forms a cap which securely seals or caps the distal portion, including the tip, of a needle. Thus, even in the unlikely event that the integrity of housing 14 is breached, the tip of the needle remains capped.

Figure 6:
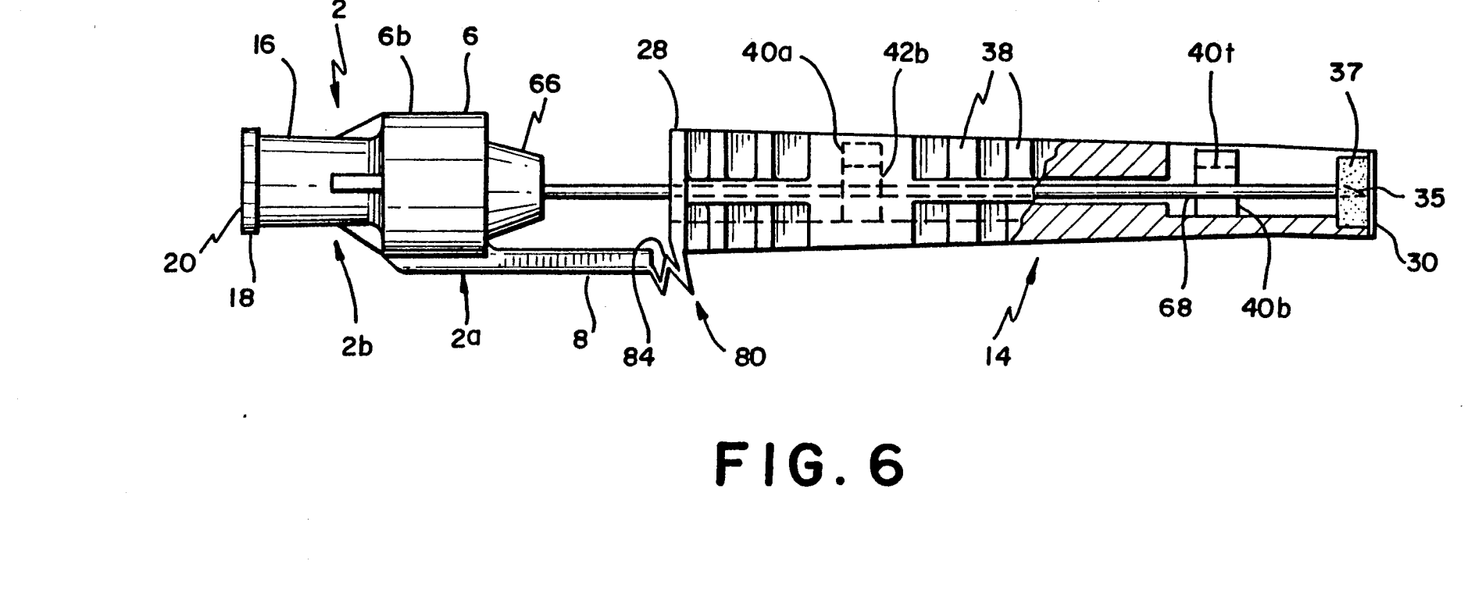
FIG. 6 is a semi-exploded side view of the FIG. 5A embodiment shown with the housing having been pivoted to align with the base and the tip of a partially-shown needle having pierced and being retained by an elastomer in the end cap section of the housing.

As for the case where a compressible joint such as 80 in FIG. 5A is used, an illustration of how the tip of the cannula of a needle assembly may be securely retained is shown in FIG. 6. There, it can be seen that needle assembly 66 has been mated to base 2 and housing 14 has been pivoted about point 84 of joint 80 to align along the longitudinal axis of cannula 68 and to envelop the same. Once cannula 68 has been retained within housing 14, relative movement of housing 14 and base 2 can be effected toward each other by, for example urging tip 30 of housing 14 against some immobile object, so that tip 35 penetrates into elastomer 37 and be securely retained thereby. As shown, joint 80 provides the compressibility for which elastomer 37 may be urged toward and securely retain tip 35 of cannula 68.

With the addition of elastomeric end cap section 29, there no longer is an absolute need to use the retention mechanism shown in FIG. 1D. Instead, by only using the retention mechanism shown in FIG. 1E to frictionally hold the needle in alignment and then urge the elastomer against the tip of the needle, an adapter that provides a high level of protection for the user is effected.

As is apparent, the adapter of the present invention is meant for one-handed operation, insofar as the user only needs to first urge housing 14 against an immobile object to pivot about base 2 to envelop the needle and then urge tip 30 of housing 14 against possibly the same immobile object to sealingly secure the tip of the needle.

For the FIG. 3 illustration, if the embodiment of the safety adapter of FIG. 2A is to be used in place of that shown in FIG. 1A, the same slip-fit mating of male luer 62 and female luer 2b discussed earlier remains true. But in addition to that, conical extension (male luer) 50 within female luer 2b of base 2 (See FIG. 2A) is now inserted through hole 73 into male luer 62 of syringe 60. And inasmuch as through bore 52 (see FIG. 2A) has substantially the same diameter as the bore of cannula 68 and thus in effect provides a direct path from syringe 60 into hub 66 of needle assembly 64, the volume of space through which a fluid transits between syringe 60 and cannula 68 is substantially reduced. In other words, the dead space volume in a conventional connection between the hub of a needle assembly and the male luer of a syringe is substantially reduced.

In FIG. 4, there is shown a luer lock type syringe 72 which has an internally threaded collar 76 surrounding its male luer (ejection end) 74. The mating of hub 66 of needle assembly 64 to section 2a of base 2 is as was discussed with reference to FIG. 3 and therefore will not be further discussed herein. As for the mating of section 2b to male luer 74, with the addition of annular collar 76, extension 18 at the distal end of section 2b (See FIG. 2A) is now used to threadedly mate with thread 78 at the inner circumference of collar 76. Male luer 74 of course will remain slip-fittedly mated with section 2b, if the safety adapter shown in FIG. 1A is used. If, instead, the safety adapter shown in FIG. 2A is used, then in addition to slip fitting along sides 22a and 22b (see FIG. 2A) of section 2b, the interior of male luer 74 will also be mated with conical extension 50 so that dead space volume will be reduced.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

I claim:

1. Safety device to be used with a needle, comprising:
   a base for connecting said needle to a syringe;
   a housing having a first selection flexibly coupled to said base, a second section longitudinally in alignment with said baseand a compressible section sandwiched between and integrally connecting said first and second sections, said housing pivotable about said base toward a position in substantial alignment along the longitudinal axis of said needle for enveloping said needle; and
   means adapted to said second section to substantially sealingly secure the tip of said needle when said second section is urged toward said first section.

2. Safety device of claim 1, wherein said sealingly secure means comprises an elastomeric material for firmly gripping the tip of said needle after said elastomeric material has been urged against said needle and penetrated thereby. gripping the tip of said needle after said elastomeric material has been urged against said needle and penetrated thereby.

3. Safety device of claim 1, wherein said housing comprises an elongated slot through which said needle passes when said housing is pivoted to said position, said elongated slot extending at least from said first section to said compressible section.

4. Safety device of claim 1, wherein said compressible section comprises a semi-enclosed extension fixedly connecting said first section to said second section, said extension collapsible when said second section is urged toward said first section to enable the tip of said needle to penetrate said sealingly secure means and be firmly gripped thereby.

5. Safety device of claim 1, wherein said first section of said housing is flexibly coupled to said base by a living hinge.

6. Safety device of claim 1, further comprising:
   means in said housing for retaining said needle within said housing once said housing has been pivoted to said position.

7. Safety device of claim 6, wherein said sealingly secure means comprises an elastomeric material for firmly gripping the tip of said needle after said elastomeric material has been urged against said needle and penetrated thereby.

8. Safety device of claim 6, wherein said retaining means comprises a hooking means integral of said housing for securely confining said needle within said housing to prevent relative movement between said needle and said housing.

9. Safety device of claim 6, wherein said retaining means comprises a plurality of hooking means integrated to said housing for securely confining said needle within said housing to prevent relative movement between said needle and said housing.

10. Safety device of claim 6, wherein said retaining means comprises at least one forked means for frictionally holding said needle within said housing.

11. Safety device of claim 1, wherein said needle is integrated to a hub and wherein said base comprises:
    a first portion including a protrusion and securing means substantially surrounding said protrusion for providing secured mating of said protrusion to said hub of said needle;
    a second portion integrated to said first portion extending from said securing means and having means for mating with an ejection end of said syringe.

12. Safety device of claim 11, wherein said securing means comprises an annular collar having at its inner circumference threads for accepting said hub of said needle.

13. Safety device of claim 11, wherein said mating means of said second portion comprises a bore extending substantially throughout said second portion for slip-fittedly mating with said ejection end of said syringe.

14. Safety device of claim 11, wherein said mating means of said second portion comprises means at the distal end of said second portion for threadedly mating with an internally threaded collar surrounding said ejection end of said syringe.

15. Safety device of claim 11, further comprising:
    an internal bore taperedly extending throughout said protrusion and said second portion to provide a direct passage for fluid transiting between said ejection end of said syringe and said needle hub.

16. Safety device of claim 11, wherein said protrusion of said first portion has a through bore substantially the size of the bore of said needle; and
    wherein said second portion has a conical extension projecting away from said protrusion having a through bore substantially matching the size of the through bore of said protrusion, the respective through bores of said protrusion and said conical extension effecting one continuous through bore in said base; and
    wherein said conical extension is inserted into said ejection end of said syringe when said second portion is mated to said ejection end for substantially reducing the volume of space through which fluid transits between said syringe and said needle.

17. Safety device to be used with a needle, comprising:
    a base having integral first and second portions for coupling said needle to a syringe;
    housing means having a main section one end of which being flexibly connected to said first portion of said base, an end section and a compressible section sandwiched between said main and end sections, said housing means pivotable about said first portion of said base to an operative position to substantially align along the longitudinal axis of said needle for enveloping the same;
    means adapted to said end section of said housing means to sealingly secure the tip of said needle after said needle has been enveloped by said housing means and said end section has been urged toward said base such that said compressible section collapses longitudinally along the length of the needle.

18. Safety device of claim 17, wherein said sealingly secure means comprises an elastomeric material for firmly gripping the distal end of said needle including its tip as said end section is urged toward said base and said elastomeric material is penetrated by said needle.

19. Safety device of claim 17, wherein said first portion of said base comprises a male luer for mating with a hub of said needle; and wherein said first portion further comprises an internally threaded annular collar surrounding said male luer for threadingly securing said needle hub thereto, thereby detachably coupling said needle to said first portion.

20. Safety device of claim 17, wherein said second portion of said base comprises a female luer for slip-fittedly mating with an ejection end of said syringe.

21. Safety device of claim 17, wherein said second portion of said base comprises a luer locking hub for threadedly mating with an internally threaded collar surrounding an ejection end of said syringe.

22. Safety device of claim 17, wherein said housing means comprises an elongated slot extending at least along the length of said main section, said needle passing through said slot when said housing means is pivoted to said operative position.

23. Safety device of claim 17, wherein said base comprises a male luer at said first portion for mating to a hub of said needle;

wherein said base further comprises a snout extending to said second portion, a bore having a diameter substantially the size of that of the bore of said needle extending through said male luer and said snout; and wherein, when said snout is inserted into an ejection end of said syringe, the fluid directly transits between said syringe and said needle through said bore extending through said male luer and said snout.

24. Safety device of claim 17, wherein said compressible section is made thinner than said main section such that, when said end section is urged toward said base, said compressible section collapses longitudinally along the length of said needle to thereby enable said means adapted to said end section to sealingly secure the tip of said needle.

25. Safety device of claim 17, wherein said compressible section comprises a semi-enclosed extension integrally connecting said main section to said end section of said housing, said extension foldable when said end section is urged toward said base to enable the tip of said needle to penetrate said sealingly secure means and be firmly gripped thereby.

26. Safety device of claim 17, further comprising:
means integrated in said housing means for substantially preventing said needle from moving relative to said housing means when said housing means has been pivoted to said operative position.

27. Safety device of claim 26, wherein said sealingly secure means comprises an elastomeric material for firmly gripping the distal end of said needle including its tip as said end section is urged toward said base and said elastomeric material is penetrated by said needle.

28. Safety device of claim 26, wherein said preventing means comprises a substantially rigid hook means integral of said housing.

29. Safety device of claim 26, wherein said preventing means comprises a plurality of hooking means integral of said housing.

30. Safety device of claim 26, wherein said preventing means comprises at least one forked means for frictionally holding said needle.

31. Safety device for a needle having a hub, comprising:
a base having
a first portion including a male projection for insertion into said hub of said needle, and an internally threaded annular collar surrounding said male projection for detachably coupling said needle to said base via said hub;
a second portion integrally extending away from said first portion including a female receptacle for accepting an ejection end of a syringe; and
a housing pivotable to a position in substantial alignment along the longitudinal axis of said needle for enveloping said needle, said housing having
a main body one end of which being flexibly connected to said first portion of said base to provide pivoting thereabout;
an end cap;
a compressible extension sandwiched between said main body and said end cap, and integrally connecting the other end of said main body to said end cap; and
means within said main body for confining said needle within said housing once said housing has been pivoted to said position.

32. Safety device of claim 31, further comprising:
grip means adapted to said end cap to securely grip the tip of said needle after said housing has been pivoted to said position to envelop said needle and a force being applied against said end cap to compress said compressible extension to force the tip of said needle to penetrate said grip means.

33. Safety device of claim 31, further comprising:
a snout integrated to said second portion axially positioned within said female receptacle and extending to the distal end of said second section for insertion into said ejection end of said syringe;
a through bore having a diameter substantially the size of that of the bore of said needle extending through said male projection and said snout;
wherein, when said snout is inserted into said ejection end of said syringe, fluid transiting between said syringe and said needle only passes through said through bore for substantially reducing the volume of space through which said fluid needs to transit.

34. Safety device of claim 31, wherein said housing comprises an elongated slot extending at least along the length of said main body, said needle passing through said slot when said housing is pivoted to said position.

35. Safety device of claim 31, wherein said confining means comprises a hooking means integral of said main body of said housing for retaining said needle within said housing to prevent relative movement between said needle and said housing.

36. Safety device of claim 31, wherein said confining means comprises a plurality of hooking means integrated into said main body of said housing for securely retaining said needle within said housing to prevent relative movement between said needle and said housing.

37. Safety device of claim 31, wherein said confining means comprises at least one forked means integral of said main body for frictionally holding said needle within said housing.

38. Safety device of claim 31, wherein said grip means comprises an estomeric material.

39. Safety device to be used with a needle, comprising:
- a base for connecting said needle to a syringe;
- a housing having a first end and a second end;
- compressible joint means flexibly connecting said housing to said base via said first end, said housing pivotable about said joint means toward a position in substantial alignment along the longitudinal axis of said needle for enveloping said needle; and
- means adapted to said second end to sealingly secure the tip of said needle when a compressive force resulting from a relative movement of said housing and said base being urged toward each other is applied to said joint means to compress the same.

40. Safety device of claim 39, wherein said joint means comprises a compressible hinge integrally connecting said first end of said housing to said base.

41. Safety device of claim 39, wherein said joint means comprises a compressible hinge integrally connecting said first end of said housing to a shoulder member extending from said base.

42. Safety device of claim 39, wherein said sealingly secure means comprises an elastomeric material for firmly gripping the tip of said needle after said elastomeric material has been urged against said needle and penetrated thereby.

43. Safety device of claim 39, wherein said housing comprises an elongated slot through which said needle passes when said housing is pivoted to said position.

44. Safety device of claim 39, further comprising:
- means in said housing for retaining said needle within said housing once said housing has been pivoted to said position.

45. Safety device of claim 44, wherein said retaining means comprises a hooking means integral of said housing for 3 securely confining said needle within said housing to prevent relative movement between said needle and said housing.

46. Safety device of claim 44, wherein said retaining means comprises a plurality of hooking means integrated to said housing for securely confining said needle within said housing to prevent relative movement between said needle and said housing.

47. Safety device of claim 44, wherein said retaining means comprises at least one forked means for frictionally holding said needle within said housing.

48. Safety device of claim 50, further comprising:
- an internal bore taperedly extending throughout said protrusion and said second portion to provide a direct passage for fluid transiting between said ejection end of said syringe and said needle hub.

49. Safety device of claim 50, wherein said protrusion of said first portion has a through bore substantially the size of the bore of said needle; and
- wherein said second portion has a conical extension projecting away from said protrusion having a through bore substantially matching the size of the through bore of said protrusion, the respective through bores of said protrusion and said conical extension effecting one continuous through bore in said base; and
- wherein said conical extension is inserted into said ejection end of said syringe when said second portion is mated to said ejection end for substantially reducing the volume of space through which fluid transits between said syringe and said needle.

50. Safety device of claim 39, wherein said needle is integrated to a hub and wherein said base comprises:
- a first portion including a protrusion and securing means substantially surrounding said protrusion for providing secured mating of said protrusion to said hub of said needle;
- a second portion integrated to said first portion extending from said securing means and having means for mating with an ejection end of said syringe.

51. Safety device of claim 50, wherein said securing means comprises an annular collar having at its inner circumference threads for accepting said hub of said needle.

52. Safety device of claim 50, wherein said mating means of said second portion comprises a bore extending substantially throughout said second portion for slip-fittedly mating with said ejection end of said syringe.

53. Safety device of claim 50, wherein said mating means of said second portion comprises means at the distal end of said second portion for threadedly mating with an internally threaded collar surrounding said ejection end of said syringe.

54. Safety device to be used with a needle, comprising:
- a base having integral first and second portions for coupling said needle to a syringe;
- a housing having a first end and a capped end;
- compressible means flexibly coupling said first end of said housing to said second portion of said base so that said housing is pivotable about said compressible means to an operative position to substantially align along the longitudinal axis of said needle for enveloping the same;
- means adapted to said capped end of said housing to sealingly secure the tip of said needle after said housing has been pivoted to envelop said needle and said housing and said base urged relative toward each other to compress said compressible means longitudinally along the length of said needle.

55. Safety device of claim 54, wherein said compressible means comprises a collapsible living hinge connecting said first end of said housing to a shoulder member extending from said second portion of said base.

56. Safety device of claim 54, further comprising:
- means in said housing for retaining said needle within said housing once said housing has been pivoted to said position.

57. Safety device of claim 54, wherein said sealingly secure means comprises an elastomeric material for firmly gripping the tip of said needle after said elastomeric material has been urged against said needle and penetrated thereby.

* * * * *